US010209211B2

(12) United States Patent
Werk et al.

(10) Patent No.: US 10,209,211 B2
(45) Date of Patent: Feb. 19, 2019

(54) METHOD FOR DETERMINING WHETHER RECONSTITUTION OF A SOLUTION IN A CONTAINER IS COMPLETED

(71) Applicant: Hoffmann-La Roche Inc., Little Falls, NJ (US)

(72) Inventors: Tobias Werk, Riehen (CH); Jörg Lümkemann, Lörrach (DE); René Rietmann, Kaiseraugst (CH); Roger Steiner, Allschwil (CH); Hanns-Christian Mahler, Basel (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 162 days.

(21) Appl. No.: 15/321,508

(22) PCT Filed: Jun. 26, 2015

(86) PCT No.: PCT/EP2015/064477
§ 371 (c)(1),
(2) Date: Dec. 22, 2016

(87) PCT Pub. No.: WO2015/197807
PCT Pub. Date: Dec. 30, 2015

(65) Prior Publication Data
US 2017/0212068 A1 Jul. 27, 2017

(30) Foreign Application Priority Data

Jun. 27, 2014 (EP) .................................... 14174830

(51) Int. Cl.
*G01N 27/07* (2006.01)
*G01N 27/06* (2006.01)
(Continued)

(52) U.S. Cl.
CPC ............. *G01N 27/07* (2013.01); *G01N 13/00* (2013.01); *G01N 27/06* (2013.01); *G01N 33/15* (2013.01); *G01N 2013/006* (2013.01)

(58) Field of Classification Search
USPC ....................... 324/693, 663, 612, 609, 71.1
See application file for complete search history.

(56) References Cited

U.S. PATENT DOCUMENTS

| 3,618,395 A | 11/1971 | Melliger |
| 2003/0159947 A1 | 8/2003 | Tajiri et al. |

(Continued)

FOREIGN PATENT DOCUMENTS

| CN | 1057109 A | 12/1991 |
| CN | 1439874 A | 9/2003 |

(Continued)

OTHER PUBLICATIONS

Rimpilä Inen Ville et al: "An electrical impedance tomography-based approach to monitor vitro sodium chloride dissolution from pharmaceutical tablets", Review of Scientific Instruments, AIP, Melville, NY, US, vol. 80, No. 10, Oct. 21, 2009 (Oct. 21, 2009), pp. 103706-103706.

(Continued)

*Primary Examiner* — Vincent Q Nguyen
(74) *Attorney, Agent, or Firm* — Mintz Levin Cohn Ferris Glovsky and Popeo, P.C.

(57) ABSTRACT

A method for determining whether reconstitution of a solution in a container is completed comprises the steps of:
selecting a predetermined amount of a solid substance and a predetermined amount of a liquid solvent from which the reconstituted solution is to be prepared,
preparing a solution by solving the predetermined amount of the solid substance in the predetermined amount of the liquid solvent, (Continued)

measuring the impedance (Z) or the resistance (R) of the solution,
determining whether the change of the measured impedance (Z) or the resistance (R) within a measuring time interval of a predetermined duration is below a defined threshold, and
determining that reconstitution of the solution is completed when the change of the measured impedance (Z) is below the defined threshold.

14 Claims, 5 Drawing Sheets

(51) Int. Cl.
    *G01N 33/15*      (2006.01)
    *G01N 13/00*      (2006.01)

(56) References Cited

U.S. PATENT DOCUMENTS

2009/0240442 A1    9/2009   Zeng
2016/0331682 A1*   11/2016   Payet-Burin ......... A61K 9/0095

FOREIGN PATENT DOCUMENTS

| CN | 101017147 A | 8/2007 |
| CN | 102141531 A | 8/2011 |
| DE | 29711454 U1 | 10/1997 |
| DE | 102009031859 A1 | 1/2011 |

OTHER PUBLICATIONS

International Search Report Issued in PCT/EP2015/064477 dated Oct. 14, 2015.
Funke, K et al. "Apparative Methoden in der Physikalischen Chemie." Impedeanzspektroskopie, Institut fur Physikalische Chemie Munster. vol. 9 (2002): pp. 1-13.
English Abstract of CN 1439874 A.
English Abstract of CN 101017147 A.
English Abstract of CN 102141531 A.

* cited by examiner

METHOD FOR DETERMINING WHETHER RECONSTITUTION OF A SOLUTION IN A CONTAINER IS COMPLETED

CROSS-REFERENCE TO RELATED APPLICATIONS

This application is a national stage application, filed under 35 U.S.C. § 371, of International Application No. PCT/EP2015/064477 filed on Jun. 26, 2015, which claims priority to European Patent Application No. 14174830.1 filed on Jun. 27, 2014, the contents of each of which are hereby fully incorporated by reference.

FIELD

The present invention relates to a method for determining whether reconstitution of a solution in a container is completed.

BACKGROUND

Many solutions prepared from one or more solid substances (in the following referred to as 'a solid substance') and one or more liquid solvents (in the following referred to as 'a liquid solvent') are not sufficiently stable for being stored over an extended period of time. For example, this holds for certain solutions to be injected into a patient, such solutions containing one or more active pharmaceutical ingredients (in the following referred to as 'an active pharmaceutical ingredient'), but is of course not limited to this field of application. An active pharmaceutical ingredient is a substance in a drug that is biologically active. For example the active pharmaceutical ingredient causes the direct effect on the disease diagnosis, prevention, treatment or cure, and may comprise one or more proteins, antibodies, small molecules, etc. The active pharmaceutical ingredient may be provided as a soluble solid substance. This soluble solid substance may or may not contain additional excipients, and can be stably stored over extended periods of time. When the time has come to administer the active pharmaceutical substance, it is then to be solved in the liquid solvent (e.g. water for injection, saline solution or another liquid solvent for injection which may or may not contain an additional active pharmaceutical ingredient in order to yield the definitive solution before administering, e.g. injecting, infusing etc. to the patient.

The solid substances comprising the active pharmaceutical ingredient are often obtained through lyophilisation. Other common ways to obtain solid substances are spray drying and other drying processes known in the art. Lyophilization is often used because it is a gentle process of obtaining the solid substance containing the active pharmaceutical ingredient. Solid substances obtained through lyophilisation can be stably stored in a container in the form of powder or granules, or in the form of a compact cake, and are typically soluble in the liquid solvent (e.g. water for injection, saline, or other diluents). Accordingly, due to the solubility of the lyophilised solid substance comprising the active pharmaceutical ingredient, the solution to be administered to the patient can be easily obtained by completely solving the lyophilized soluble solid substance in the liquid solvent, for example water for injection. The solution obtained in this manner is commonly referred to as a 'reconstituted solution'.

Regulatory frameworks require that a solution to be injected into a patient is free of visible particles. In other words, the solid substance must be visually completely dissolved in the liquid solvent before the solution is allowed to be injected into the patient. Any administration of solid material needs to be avoided. Regulatory frameworks additionally require that reconstitution of the solution to be injected is performed in the primary packaging container, which may be, for instance, a vial, a syringe (e.g. a dual chamber syringe), or an ampoule. Reconstitution can also in certain cases be performed in other relevant containers. Additionally, lyophilized powder or cake may be dissolved for further processing and not for final administration to patients. Examples include freeze-drying of active ingredient with or without additional excipients. Final dissolution of the solid material is also expected and required in that case.

Accordingly, the instructions provided by the manufacturer providing the predetermined amount of the solid substance containing the active pharmaceutical ingredient include the predetermined amount and type of the liquid solvent (e.g. water for injection) to be used in case the liquid solvent is not provided by the manufacturer itself together with the solid substance containing the active pharmaceutical ingredient. In addition, these instructions include the so-called 'reconstitution time'. The reconstitution time is the duration between the time of starting to solve the predetermined amount of the solid substance in the predetermined amount of the liquid solvent and the time reconstitution of the solution is completed, so that the solution has formed the reconstituted solution which does not contain any undissolved material.

Additional instructions may be provided for the preparation of the reconstituted solution, such as the temperature of the solid substance and/or the temperature of the liquid solvent and/or the temperature of the container in which the reconstituted solution must be prepared, as well as instructions related to a movement pattern of the container during solving the solid substance in the liquid solvent (e.g. a movement pattern comprising time intervals during which the container must be shaken, interrupted by time intervals in which the container is not moved).

To be able to provide these instructions, it must be determined when reconstitution of a solution is completed to allow for determination of the reconstitution time. This is presently performed by human individuals through visual inspection of the solution prepared by solving the predetermined amount of the solid substance in the predetermined amount of the liquid solvent (e.g. water for injection) in the container with a given and defined reconstitution procedure. This usually means that a plurality of individuals determine the duration between the time of starting to solve the predetermined amount of the solid substance in the predetermined amount of liquid solvent until the time there are no undissolved visible solid materials or particles contained in the reconstituted solution anymore. As is evident, this is greatly influenced by the individual visual perception of the humans and, consequently, different humans may come to very different results as regards the reconstitution time.

As mentioned, the manufacturer of the active pharmaceutical ingredient typically specifies the reconstitution time (and potentially other relevant parameters, see above) in the instructions provided together with the active pharmaceutical ingredient. To be on the safe side, the manufacturer—taking the different reconstitution times determined by the human individuals into account—must specify in the instructions (besides potential other relevant parameters) a reconstitution or holding time which is sufficiently long to make sure that indeed reconstitution of the solution is completed after the reconstitution time, so that there are no undissolved visible solid particles contained in the solution anymore. For lyophilized products containing significant amount of solid and protein, this reconstitution procedure can take up to 15 to 40 minutes.

SUMMARY

The present invention suggests a method for determining whether reconstitution of a solution in a container is completed. The method comprises the steps of:

selecting a predetermined amount of a solid substance and a predetermined amount of a liquid solvent from which the reconstituted solution is to be prepared, the predetermined amount of the solid substance and of the liquid solvent being selected such that the reconstituted solution is below its saturation limit, preparing a solution by solving in the container the predetermined amount of the solid substance in the predetermined amount of the liquid solvent, measuring a value chosen from impedance or resistance of the solution in the container, determining whether a change of the measured value within a measuring time interval of a predetermined duration is below a defined threshold, and determining that reconstitution of the solution is completed and that the reconstituted solution is formed when the change of the measured value within the measuring time interval of the predetermined duration is below the defined threshold.

In accordance with one aspect of the method according to the invention, the measured value is the impedance of the solution.

In accordance with another aspect of the method according to the invention, the measured value is the resistance of the solution.

In accordance with yet another aspect of the invention, the change of the measured value within the measuring time interval of the predetermined duration is below the threshold of 0.01%-5%.

In accordance with another advantageous aspect of the method according to the invention, the method further comprises the steps of:

determining a reconstitution time of the solution in the container to be the duration between the time of starting to prepare the solution and the time at which the change of the measured impedance or resistance of the solution is below the defined threshold within the measuring time interval of the predetermined duration. The point in time of "starting to prepare the solution" is herein defined as the point in time at which the whole predetermined amount of the liquid solvent has been added to the predetermined amount of solid substance to prepare the solution. Reconstitution time is measured from that point in time.

In accordance with a further advantageous aspect of the method according to the invention the solid substance to be solved in the liquid solvent comprises an active pharmaceutical ingredient. An active pharmaceutical ingredient, as mentioned above, is a substance in a drug that is biologically active. For example the active pharmaceutical ingredient causes the direct effect on the disease diagnosis, prevention, treatment or cure, and may comprise one or more proteins, antibodies, small molecules, etc.

In accordance with yet a further advantageous aspect of the method according to the invention the solid substance to be solved in the liquid solvent is a lyophilisate.

In accordance with still a further aspect of the method according to the invention, the method further comprises the step of setting the temperature of the solid substance and/or the temperature of the solvent and/or the temperature of the container to a respective predetermined temperature for preparing the reconstituted solution.

In accordance with a further aspect of the method according to the invention, the method further comprises the step of moving the container in accordance with a predetermined movement pattern during solving the solid substance in the liquid solvent.

According to a further aspect of the method according to the invention measuring the impedance or resistance of the solution in the container is performed only during portions of the movement pattern in which the container is not moved.

According to another aspect of the method according to the invention, the method further comprises the steps of:

before determining the reconstitution time of the solution prepared from the predetermined amount of the solid substance and the predetermined amount of the liquid solvent, measuring the impedances or resistances of a plurality of reconstituted solutions prepared from the same solid substance and the same liquid solvent, the individual reconstituted solutions of the plurality of reconstituted solutions having different concentrations of the solid substance solved in the respective individual reconstituted solution, from the measurement of the impedances or resistances of the plurality of reconstituted solutions determining a relationship between the impedance or resistance and the concentration of the solid substance solved in this solution, and determining the dissolution behavior over time during solving the predetermined amount of the solid substance in the predetermined amount of liquid solvent by assigning the respective measured impedance or resistance of the solution to the respective concentration in accordance with the determined relationship between the impedance or resistance and the concentration of the solid substance solved in the solution.

Yet in accordance with another aspect of the method according to the invention, the method further comprises the steps of:

before determining the reconstitution time of the solution prepared from the predetermined amount of the solid substance and the predetermined amount of the liquid solvent, measuring the impedance or resistance of each individual reconstituted solution of the plurality of reconstituted solutions at a plurality of different temperatures, and from the measurement of the impedance or resistance of the individual reconstituted solutions at the different temperatures determining a relationship between the impedance or resistance of the respective individual solution and the temperature.

In accordance with still another aspect of the method according to the invention the step of measuring in the container the impedance or resistance of the solution comprises:

providing an electrode having an electrically conductive inner tube and an electrically conductive outer tube, the outer tube surrounding the inner tube and being electrically isolated from the inner tube, arranging the distal end of the electrode comprising the distal ends of the outer tube and the inner tube in the container in a manner such that the distal ends of the outer tube and of the inner tube are immersed in the solution during determination of the reconstitution time of the solution, supplying an alternating current of a predetermined amperage to either the inner tube or the outer tube at a supply location of the electrode outside the container, measuring the amperage of the alternating current supplied to either the outer tube or the inner tube of the electrode, measuring an alternating voltage between the outer tube and the inner tube of the electrode, and calculating the impedance or resistance of the solution from the measured alternating voltage between the outer tube and the inner tube and from the measured amperage of the alternating current supplied to either the outer tube or the inner tube.

According to yet another aspect of the method according to the invention the step of preparing the solution by solving in the container the predetermined amount of the solid substance in the predetermined amount of the liquid solvent comprises the steps of:

providing in the container the predetermined amount of the solid substance, providing a feeding port at the proximal end of the inner tube of the electrode, the feeding port being in fluid communication with the interior of inner tube, and feeding the predetermined amount of the liquid solvent through the feeding port and the interior of the inner tube into the container to prepare the solution in the container.

The method according to the invention offers a plurality of advantages. For example, the method according to the invention allows for an automated determination whether reconstitution of a solution is completed, and thus eliminates any subjective perception or assessment of a human individual as to whether or not there are any visible solid particles contained in the solution. If the measured change in impedance or resistance within the measuring interval of the predetermined duration (for example a few seconds) is below a defined threshold, for example below a threshold of 0.01%-5% this small change in impedance or resistance of a few percent is representative of the fact that no solid material is contained in the solution anymore, otherwise the change of the impedance or resistance within the said measuring time interval is above the threshold. Therefore, the threshold for the change in impedance or resistance within the measuring time interval of the predetermined duration is an objective measure devoid of any subjective perception of a human individual. The method of the invention is also more accurate than when based on visual inspection: the method according to the invention shows a relatively narrower distribution and results in shorter reconstitution times when compared to visual inspection. Determination by human eye is highly subjective (differences between operators) and imprecise (relatively wide distributions). This subjectivity can be attributed to human eye variability. The imprecision may be explained by human end point determination procedure: the manual process involves a stopwatch to be actuated if reconstitution is finished. Operators usually look for the last residue before pressing the stopwatch. Consequently, a time is recorded that corresponds to the reconstitution time plus a time used to search a last residue and prove that none is present. The method according to the invention determines the end point based on objective measurement of physical values (impedance, resistance) and therefore eliminates the subjectivity of a human operator and minimizes the imprecisions.

Completion of the reconstitution of a solution can thus be objectively determined even without determination of the reconstitution time of the solution. For example, measurement of the impedance or resistance of the solution does not necessarily have to start at the time of starting to solve the predetermined amount of the solid substance in the liquid solvent but may start some time thereafter. In principle, it is even possible to measure the impedance or resistance of the solution after reconstitution of the solution is already completed. In this case, the measurement of the impedance or resistance of the solution just confirms that reconstitution of the solution is completed by measuring a change of the impedance or resistance which is smaller than the defined threshold within the measuring time interval of the predetermined duration.

It is to be noted, however, that it is a requirement that the predetermined amount of the solid substance and the predetermined amount of the liquid solvent be selected such that the reconstituted solution (the solution in which the predetermined amount of the solid substance is completely dissolved in the predetermined amount of the liquid solvent) is below the saturation limit of the solution. Since the electrical charge of ions in solution facilitates the conductance of electrical current, the impedance and resistance of a solution are highly (but not totally) proportional to its ion concentration: As concentration rises the ions may become so numerous that they impede their movement through the solution. At some point, the signal may reach a minimum and then decrease for further increase in concentration. For the application of reconstitution endpoint detection as well as for kinetic measurements impedance/resistance must either increase or decrease with concentration.

If a maximum or minimum is present in the desired concentration range, impedance/resistance signal levels off, concentration cannot be measured and end point detection of the dissolving solid substance may be biased. If the saturation limit of the solution or an extreme in the relationship signal to concentration is reached before the predetermined amount of solid substance is completely dissolved in the liquid solvent, the change of the measured impedance or resistance may also be below the defined threshold (e.g. below 0.01%-5%) within the measuring time interval of the predetermined duration due to the solution being saturated and not being capable of dissolving the rest of the solid substance. Therefore, in order for the change in impedance or resistance below the defined threshold (e.g. below 0.01%-5%) to be representative of completion of the reconstitution of the solution, it is naturally preferable that the predetermined amount of solid substance and the predetermined amount of liquid solvent be selected such that the reconstituted solution (the solution in which the predetermined amount of the solid substance is completely dissolved in the predetermined amount of the liquid solvent) is below its saturation limit.

This would in general allow the user preparing the reconstituted solution to prepare the solution without exactly knowing the reconstitution time. For example, in one embodiment, one could use a suitable device (which will be discussed in more detail below) which is capable of indicating that the change of impedance or resistance of the solution is below the defined threshold, e.g. below the threshold of 0.01%-5%, within the measuring time interval of the predetermined duration (for example by a visual indication like a green LED or by a suitable acoustic indication) the user automatically is made aware that reconstitution of the solution is completed.

As mentioned hereinabove, it is also possible to determine the reconstitution time of a solution to be the duration between the time of starting to solve the predetermined amount of the solid substance and the time at which the change of the impedance or resistance of the solution is below the defined threshold (e.g. below 0.01%-5%) within the measuring time interval of the predetermined duration (for example a few seconds). This is of particular importance for solid substances comprising an active pharmaceutical ingredient, since the manufacturer specifies (besides other parameters) a reconstitution method and reconstitution time for the final drug to be administered and must ensure that the solid substance (e.g. the lyophilisate) is completely dissolved prior to administration. Due to this reconstitution time being determined in an automated and controlled manner, the reconstitution time can be determined with a small variation (standard deviation) of the determined reconstitution time.

This allows the manufacturer of the solid substance containing the active pharmaceutical ingredient to provide reliable instructions and to reliably test and control how the solution must be prepared to be ready for injection into the patient. The predetermined amount of the solid substance containing the active pharmaceutical ingredient may be provided in the container where it can be stably stored, such as for example in a vial, a syringe (e.g. a dual chamber syringe) or an ampoule (syringe barrel). The solution can then be prepared by introducing the predetermined amount of liquid solvent into that compartment or space of the container where the solid substance is stored. For example, in a vial, the predetermined amount of liquid solvent may be introduced through the rubber stopper of the untapped vial into the interior of the vial where the predetermined amount of the solid substance containing the active pharmaceutical ingredient is stored. In a dual chamber syringe, the predetermined amount of liquid solvent stored in one of the two storage chambers of the dual chamber syringe may be allowed to enter the other storage chamber of the dual chamber syringe where the predetermined amount of the solid substance containing the active pharmaceutical ingredient is stored. This can be achieved by the movement of a rubber stopper arranged between the two chambers of the dual chamber syringe thus generating a bypass for the liquid solvent and allowing the predetermined amount of liquid solvent to enter the chamber where the predetermined amount of the solid substance containing the active pharmaceutical ingredient is stored.

The option of setting the temperatures of the solid substance and/or of the liquid solvent and/or of the temperature of the container to a predetermined temperature for preparing the reconstituted solution allows to provide for an as short as possible and most reliable reconstitution time. Also, if the dissolution behavior of the predetermined amount of the solid substance in the liquid solvent is optimal at a known temperature, it is possible to set the temperature to this dedicated optimal temperature. In addition, the container may be moved in accordance with a predetermined movement pattern in case this is advantageous for the optimal dissolution behavior, and this movement pattern advantageously comprises portions in which the container is moved (e.g. shaken, etc.) and portions in which the container is not moved. During those portions in which the container is not moved the impedance or resistance measurement is performed, since movement of the container may have an unwanted influence on the impedance or resistance measurement.

Some embodiments of the method according to the invention allow for the determination of the kinetics of the dissolution process, in particular of the dissolution behavior of the solid substance in the liquid solvent. To obtain such information, it is useful to know the relationship between the concentration of a solution and the respective measured impedance or resistance at the said concentration of the solution. For that reason, this relationship of the impedance or resistance of a solution is determined by preparing a plurality of reconstituted solutions prepared from the same solid substance and the same liquid solvent, however, at different concentrations. The impedances or resistances of these individual reconstituted solutions are then allocated to a specific concentration of the solid substance solved in the solution. Once the relationship between the impedance or resistance of the solution and the concentration of the solid substance solved in this solution is known, the dissolution behavior over time can be determined, since once the development of the impedance/resistance over time is known from the measured impedance/resistance of the solution it is then possible to allocate the particular measured impedance/resistance to the related concentration of the solution, so that it is possible to determine the development of the concentration over time.

The impact of temperature on the impedance/resistance of a solution of a particular concentration can also be considered. For that reason, the impedance/resistance of the plurality of reconstituted solutions having different concentrations of the solid substance solved in the solution can be measured at different temperatures. Thus, it is possible to determine the relationship between temperature and impedance/resistance of each individual solution at the particular concentration of the respective solution. This allows, for example, for prediction of the reconstitution time of a solution in case the solid substance is solved in the liquid solvent at a temperature which is different from that for which the manufacturer has determined the reconstitution time.

Advantageous embodiments of the method according to the invention comprise the use of an electrode with electrically conductive outer and inner tubes which are electrically isolated from each other. The distal end of this electrode comprising the distal ends of the outer and inner tubes is arranged in the interior of the container in a manner such that the distal ends of the outer and inner tubes are immersed in the solution during determination of the reconstitution time. For example, if the container is a vial, the electrode may be pierced through the rubber stopper of the uncapped vial and the distal ends of the outer and inner tubes then project into the interior of the vial. An alternating current of predetermined amperage is then supplied to either the outer or the inner tube, and the amperage of this alternating current is measured (using an ammeter, for example). The voltage between the outer and inner tubes (the difference in the electrical potential of the outer and inner tubes) is also measured (using a voltmeter, for example), and from the measured voltage and the measured amperage the impedance/resistance of the solution is calculated as being the quotient of the measured voltage and the measured amperage. Measuring the impedance/resistance of the solution using such electrode is convenient since such electrode is a very simple device for the automatic determination of the impedance/resistance of the solution.

In case a feeding port is provided at the proximal end of the inner tube of the electrode, the predetermined amount of the liquid solvent can be introduced through the said feeding port and through the inner tube into the interior of the container, for example the vial, where the predetermined amount of the solid substance is stably stored. Accordingly, once the electrode has been properly installed (pierced through the rubber stopper) it may remain in place until reconstitution of the solution is completed.

Further advantageous aspects of the method according to the invention become apparent from the following detailed description of embodiments of the invention with the aid of the drawings in which.

DETAILED DESCRIPTION

Figure 1:
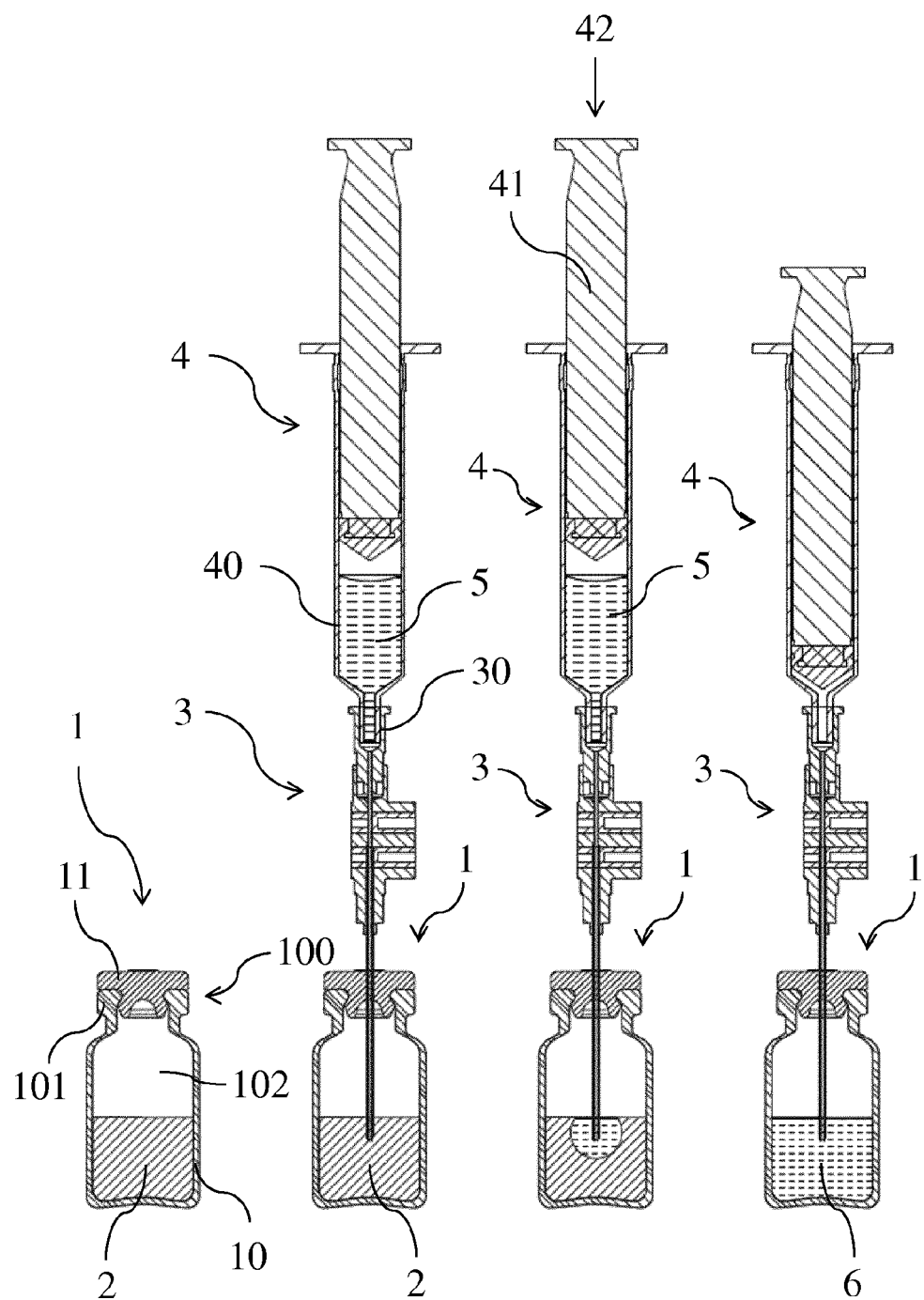
FIG. 1 shows essential steps of an embodiment of the method according to the invention during reconstitution of a solution.

In FIG. 1 some essential steps of an embodiment of the method according to the invention are shown during reconstitution of a solution. On the outermost left hand side of FIG. 1 there is shown a vial 1 representing a primary packaging container in which a predetermined amount of a solid substance 2 is stored. Solid substance 2 may be obtained through lyophilisation and may comprise an active pharmaceutical ingredient. Vial 1 comprises a glass body 10 having a neck 100 including a flange 101, with a rubber stopper 11 being pressed into the neck 100 to seal an interior space 102 of glass body 10 of vial 1 where the solid substance 2 is stored. Although not shown in FIG. 1, an aluminum cap having a centrally arranged opening in its top surface is typically crimped over flange 101 and rubber stopper 11 (engaging under the lower surface of flange 101 and over the peripheral portion of rubber stopper 11) to prevent rubber stopper 11 from being removed from the glass body 10 of the vial 1. Vial 1 in which the solid substance 2 is stored represents the container which is delivered to the customer, for example a hospital or a pharmacy.

As already mentioned hereinabove, by way of example the solution to be reconstituted may be a solution to be injected into a patient and, accordingly, a predetermined amount of a liquid solvent such as water for injection must be added to the solid substance contained in the container to form the solution to be administered, and after reconstitution of the solution is completed (no more undissolved solid material is left in the solution) the reconstituted solution can be drawn into a syringe first and thereafter be injected into the patient.

For example, the predetermined amount of liquid solvent 5 can be introduced into the interior space 102 of glass body 10 of vial 1 using a syringe the needle of which penetrates through rubber stopper 11. However, in a preferred embodiment the liquid solvent is introduced into the interior space 102 of glass body 10 of vial 1 where the predetermined amount of the solid substance 2 is stored through the inner hollow tube of an electrode 3 which is pierced through rubber stopper 11 to extend with its distal end into the solid substance 2. A feeding port 30 may be provided at the proximal end of the electrode 3, and a distal end of the syringe barrel 40 of a syringe 4 (without needle) can be connected to the feeding port 30 arranged at the proximal end of electrode 3. The predetermined amount of liquid solvent 5 is contained in the syringe barrel 40. This state is shown in the representation second from the left in FIG. 1.

To form the solution, the predetermined amount of liquid solvent 5 contained in the syringe barrel 40 is injected into the interior space 102 of the glass body 10 of vial 1 by moving a plunger 41 of syringe 4 towards the distal end of syringe 4 as indicated by arrow 42, causing the liquid solvent 5 to flow through the inner hollow tube of electrode 3 into the interior space 102 of the glass body 10 of vial 1 where the predetermined amount of the solid substance 2 is stored. Once liquid solvent 5 has entered the interior space 102 of glass body 10 of vial 1 and has come into contact with the solid substance 2 formation of the solution starts, this state being shown in the representation second from the right in FIG. 1.

The predetermined amount of the solid substance and the predetermined amount of the liquid solvent are selected such that the predetermined amount of the solid substance can be completely solved in the predetermined amount of the liquid solvent, and that the solution 6 so formed is below its saturation limit. Once the solution 6 does not contain any visible solid material anymore, the solution is fully reconstituted, this state being shown in the outermost right representation in FIG. 1.

Figure 2:
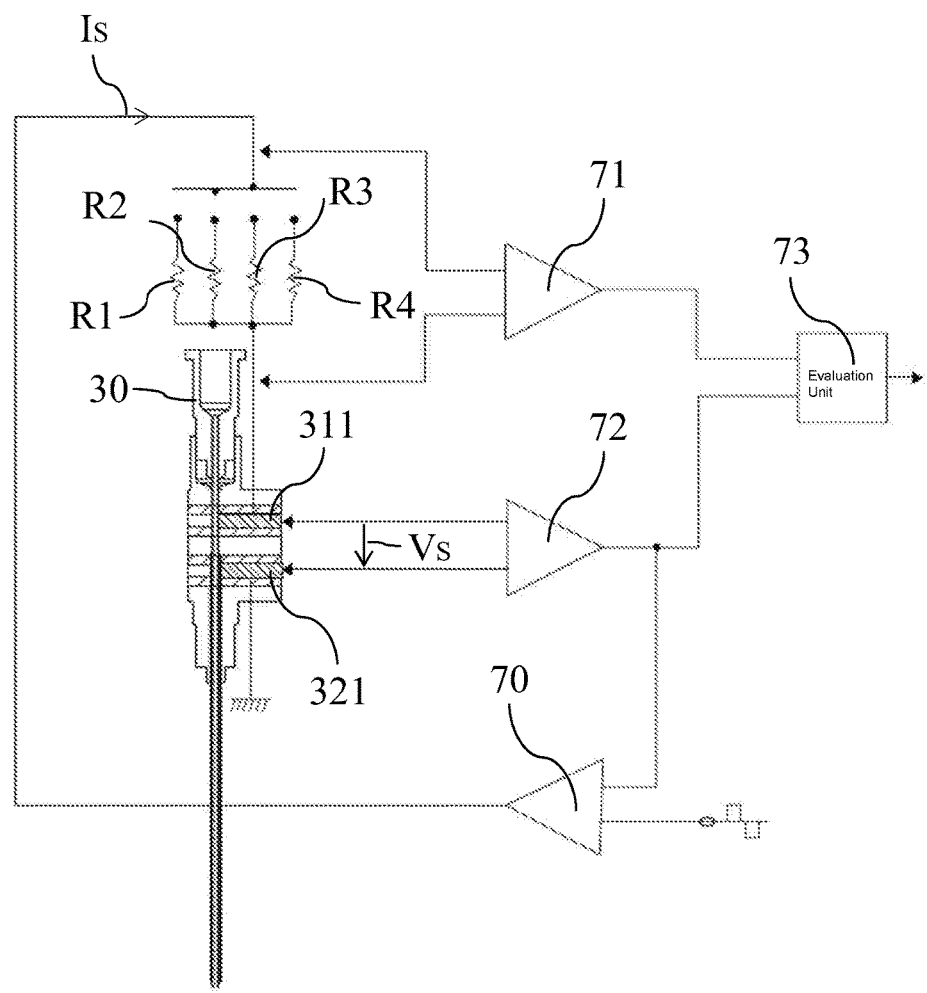
FIG. 2 shows an arrangement for measuring the impedance/resistance of the solution.
Figures 3, 4:
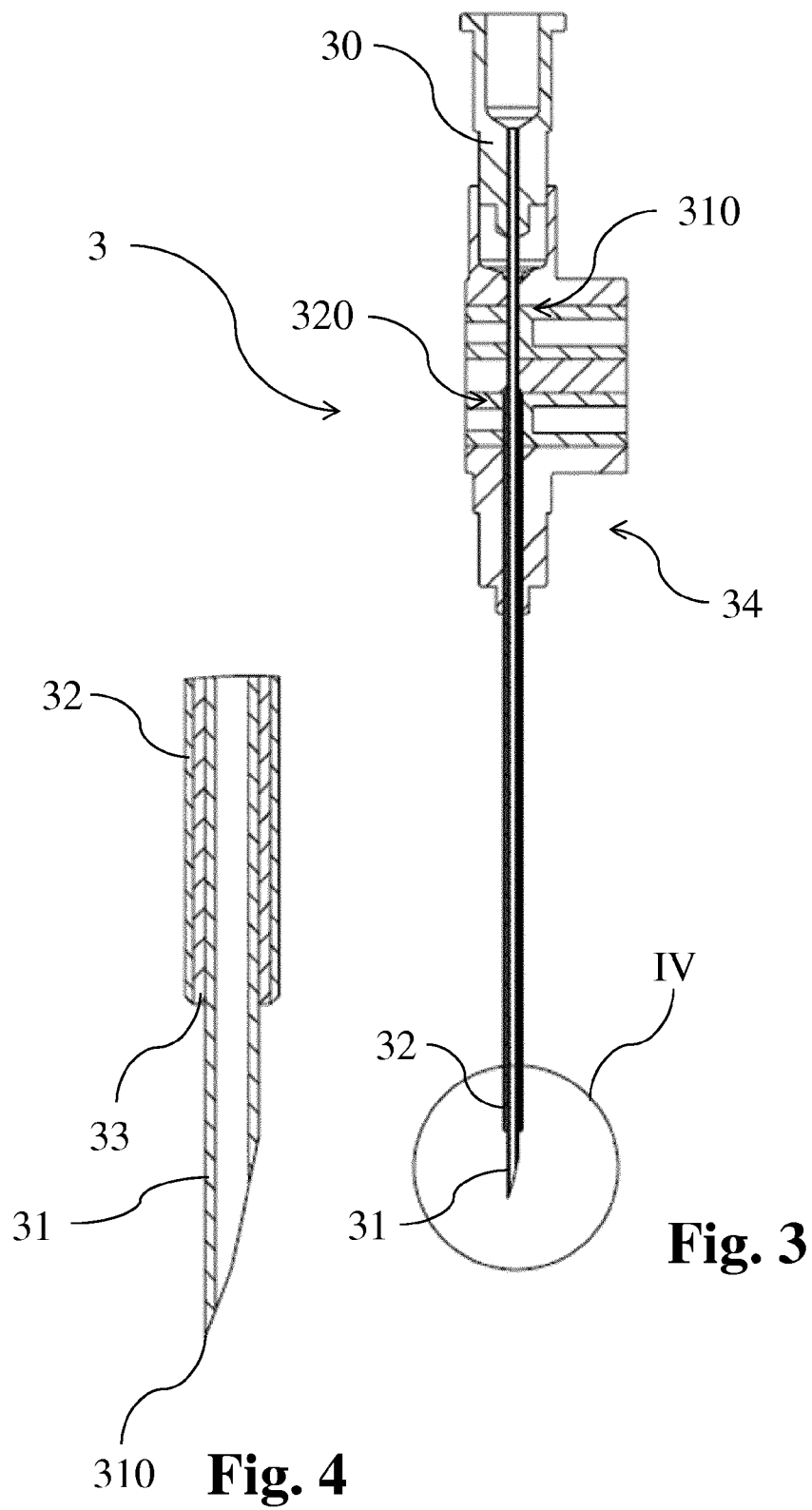
FIG. 3 shows the electrode of the arrangement of FIG. 3.
FIG. 4 shows the detail IV of FIG. 3 at the tip of the electrode.

An embodiment of an arrangement which is generally suitable to determine whether reconstitution of a solution 6 (see FIG. 1) is fully completed is shown in FIG. 2, while FIG. 3 shows the electrode 3 in an enlarged view and FIG. 4 shows the detail IV of FIG. 3 at the distal end of the electrode 3 in a still further enlarged view. As can be seen in FIG. 3, electrode 3 at its proximal end comprises the already described feeding port 30, and further comprises an electrically conductive hollow inner tube 31 as well as an electrically conductive outer tube 32 surrounding the inner tube 31. Outer tube 32 and inner tube 31 are electrically isolated from each other by an isolating cover 33 arranged radially in between inner tube 31 and outer tube 32. This can be seen even better in FIG. 4 where the distal end of electrode 3 is shown greatly enlarged. It can be seen there that the distal end of the inner tube 31 may comprise a sharp tip 312 (for simplifying penetration through the rubber stopper 11, see FIG. 1) and extends longitudinally beyond the distal end of outer tube 32. Outer tube 32 and inner tube 31 may be made from stainless steel, for example.

Returning to FIG. 3, electrode 3 comprises a housing 34 in which two electrical clamping elements are arranged, a first clamping element 310 being electrically conductively connected to inner tube 31 and a second clamping element 320 being electrically conductively connected to outer tube 32. Also, first clamping element 310 and second clamping element 320 are electrically isolated from each other in housing 34.

Returning to FIG. 2, an AC current source 70 may be provided for selectively supplying an alternating current of a predetermined frequency, which may for example be in the range of 0.1 kHz to 100 kHz, in particular in the range of 0.1 kHz to 15 kHz, to an arrangement of ohmic input impedances R1, R2, R3, and R4, the purpose of which will be explained below. The alternating supply current $I_S$ is measured using an ammeter 71 (which can also be embodied as a voltmeter, with $I_S$ being calculated from the measured voltage over the respective actual resistance R1, R2, R3 or R4 and the value of the actual R1, R2, R3, R4). Supply current $I_S$ then flows into a conductor 311 which is electrically connected to clamping element 310 (see FIG. 3) which in turn is electrically connected to inner tube 31. Supply current $I_S$ further flows through inner tube 31 into the solution 6 (see FIG. 1), through the solution 6 into outer tube 32 and back to clamping element 320 (see FIG. 3) to which a conductor 321 is connected which may be connected to ground. Clamps 310 and 320 are electrically isolated from each other. Conductors 311 and 321 are connected to a voltmeter 72 for measuring the AC voltage $V_S$ between conductors 311 and 321. The AC voltage $V_S$ between conductors 311 and 321 corresponds to the voltage drop across the solution 6 caused by the impedance Z of the solution 6, and the amplitude of the AC voltage $V_S$ can be influenced by the selective connection of one of the ohmic input impedances R1, R2, R3, and R4. The selective connection of one of the ohmic input impedances is for practical reasons, since the voltage drop across the solution should not be high, for example smaller than 1 Volt, in order to keep the power loss in the solution small so as to not heat the solution.

Generally, the impedance Z of the solution 6 can be calculated from the equation $$Z = k_i \cdot V_S / I_S$$

with $k_i$ being a constant the amount of which depends on the value of the respective actual ohmic input impedance R1, R2, R3 or R4. This calculation can be done in an evaluation unit 73 in which the respective constants $k_i$ are stored for the different values of R1, R2, R3, and R4, so that in general the impedance Z of the solution can be determined from a the measured AC voltage $V_S$ and the measured AC current $I_S$. The impedance Z generally is a complex value comprising a resistance R and a reactance jX (Z=R+jX). Although it is also possible to use the resistance R of the solution, the following explanations are given for the impedance Z.

In case reconstitution of the solution 6 is completed, that is to say the predetermined amount of the solid substance 2 is completely solved in the predetermined amount of the liquid solvent 5, the change of the impedance Z of the solution 6 is only very small. This is due to the fact that is no more undissolved material which can be solved in the solvent 5 anymore, the predetermined amount of the solid substance 2 is completely solved in the predetermined amount of the liquid solvent 5 and, accordingly, reconstitution of the solution 6 is completed.

Therefore, for practical reasons once the change of the measured impedance Z of the solution is below a defined threshold, e.g. below a threshold of 0.01%-5%, within a measuring time interval of a predetermined duration, then reconstitution of the solution 6 is completed. This predetermined duration of the measuring time interval must be selected taking the type of the solid substance 2 and the type of the liquid solvent 5 into account and must be selected such that during the measuring time interval there is surely a change of the impedance Z which is above the threshold in case there is still solid material that can be solved. Of course, as has been discussed above already, this requires that the solution is below its saturation limit so that the liquid solvent is still capable of dissolving some solid substance in case there is still any such solid substance present in the solution. Depending on the solid substance and the liquid solvent, the duration of the measuring time interval is in the range of, for example, some seconds, but may be significantly longer, as has been discussed above.

Measuring the impedance Z of the solution may generally start at any time after the predetermined amount of the liquid solvent 5 has been added to the predetermined amount of the solid substance 2. In this case, once the change of the impedance Z within the measuring time interval of the predetermined duration is below the threshold it is determined that reconstitution of the solution has been completed. It is even conceivable that the measurement of the impedance Z starts only after reconstitution of the solution 6 has been completed. In this case, after the first measuring time interval the change of the measured impedance Z is already below the threshold and, accordingly, it is determined that reconstitution of the solution 6 has been completed (which is correct).

It is also possible to determine the reconstitution time of the solution 6. In this case, the measurement of the impedance Z starts once the predetermined amount of the liquid solvent 5 has been added to the predetermined amount of the solid substance 2 in the container, and once the change in impedance Z of the solution within the measuring time interval of the predetermined duration is below the threshold it is determined that reconstitution of the solution 6 is completed. The duration between the start of the measurement of the impedance Z and the time at which the change of the measured impedance Z is below the threshold is determined to be the reconstitution time of the solution 6. In this case, it is conceivable that the evaluation unit 73 comprises an indication (e.g. a green LED) signaling that reconstitution of the solution has been completed, and may comprise a display showing the determined reconstitution time.

Figure 5:
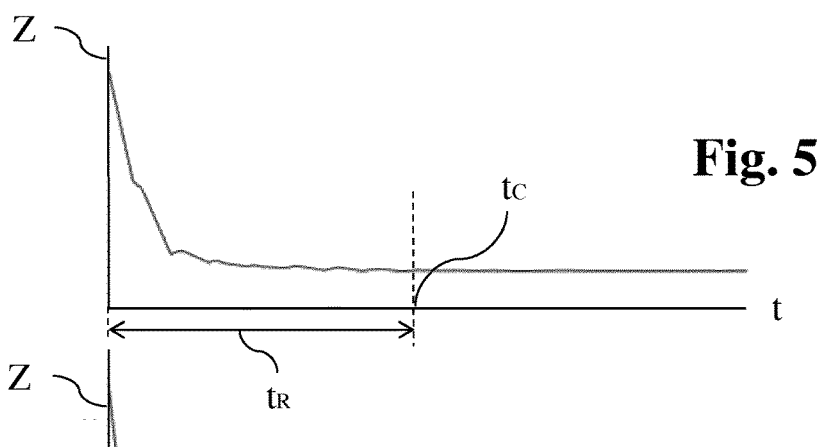
FIG. 5 shows an embodiment of the measured impedance Z of the solution over time.

FIG. 5 shows a graph representing an embodiment of the development of the impedance Z of a solution over time t. Let us assume that the measurement of the impedance Z of the solution starts at the time the predetermined amount of liquid solvent 5 has been added to the predetermined amount of the solid substance 2 to form the solution. As more solid substance 2 is getting dissolved in the liquid solvent 5 the impedance Z of the solution decreases due to the solution getting more conductive. At the time $t_C$ the change of the measured impedance Z is below the defined threshold during the measuring time interval and, accordingly, at this time $t_C$ reconstitution of the solution 6 has been completed. The duration between the time of starting to prepare the solution (in FIG. 5 the time zero, generally the time at which the predetermined amount of liquid solvent has been added to the predetermined amount of solid substance) is determined to be the reconstitution time $t_R$ of the solution.

The reconstitution time $t_R$ taken alone, however, does not contain any information about the dissolution behavior, that is to say, the reconstitution time $t_R$ does not contain any information as to whether dissolution progresses rapidly at the beginning and then slows down or progresses in a different manner. This is because the relationship between the measured impedance Z and the concentration of the solid substance dissolved in the liquid solvent is not known. Accordingly, in order to obtain information on the dissolution behavior the relationship between the impedance Z of the solution and the concentration c has to be determined.

Figure 6:
FIG. 6 shows an embodiment of the impedance Z over the concentration of the solid substance solved in the solution.

This can be done, for example, by measuring the impedances Z of a plurality of reconstituted solutions prepared from the same solid substance 2 and the same liquid solvent 5, however, at different concentrations c. Thus, the relationship between the impedance Z of the individual reconstituted solution and the corresponding concentration c can be determined. Since this is done for a plurality of individual reconstituted solutions each having a different concentration c, the relationship between the impedance Z and the concentration c can be determined. A typical relationship between the impedance Z and the concentration c is represented in the graph shown in FIG. 6.

Figure 7:
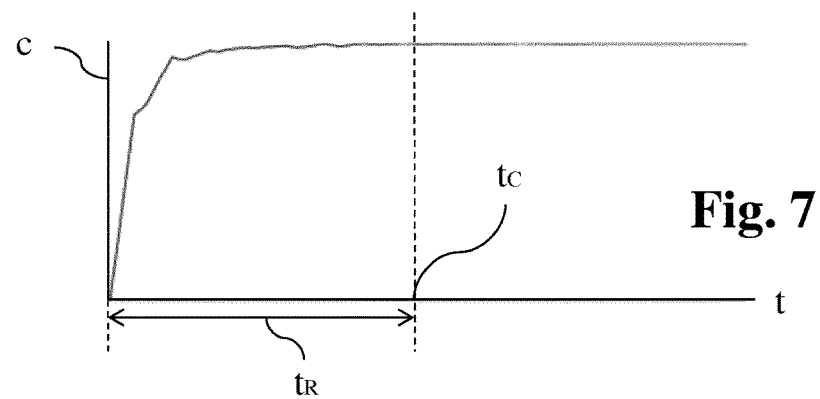
FIG. 7 shows an embodiment of the concentration of the solid substance solved in the solution over time.

Once the relationship between the impedance Z and the concentration c is known, the dissolution behavior over time (concentration c over time t) can be determined by assigning the respective measured impedance Z of the solution to the respective concentration which is known from the already determined relationship between the impedance Z and the concentration. A graph representing the dissolution behavior (concentration c over time t) is shown in FIG. 7.

This dissolution behavior can be directly determined from the measured impedance Z of the solution provided that the relationship between the impedance Z and the concentration is already known at the time of measuring the impedance Z of the solution. For example, this relationship between the impedance Z and the concentration c has been determined (for the same solid substance 2 and the same liquid solvent 5) and is stored in the evaluation unit 73 before the measurement of the impedance Z of a solution 6 prepared from a predetermined amount of the solid substance 2 and the liquid solvent starts.

Another aspect relates to the fact that the impedance Z of a solution having a specific concentration may vary depending on the temperature of the solution. In this case, the afore-mentioned determined dissolution behavior of the solid substance in the liquid solvent only holds for the respective temperature at which the solution is prepared. Or to say it in other words, the dissolution behavior and the reconstitution time may vary depending on the temperature at which the solution is prepared.

For that reason, when measuring the impedances Z of a plurality of individual reconstituted solutions each having a different concentration (to determine the relationship between the concentration of a solution and the corresponding impedance), this measurement of the impedances Z of the individual solutions is preferably performed at a plurality of different temperatures.

Figure 8:
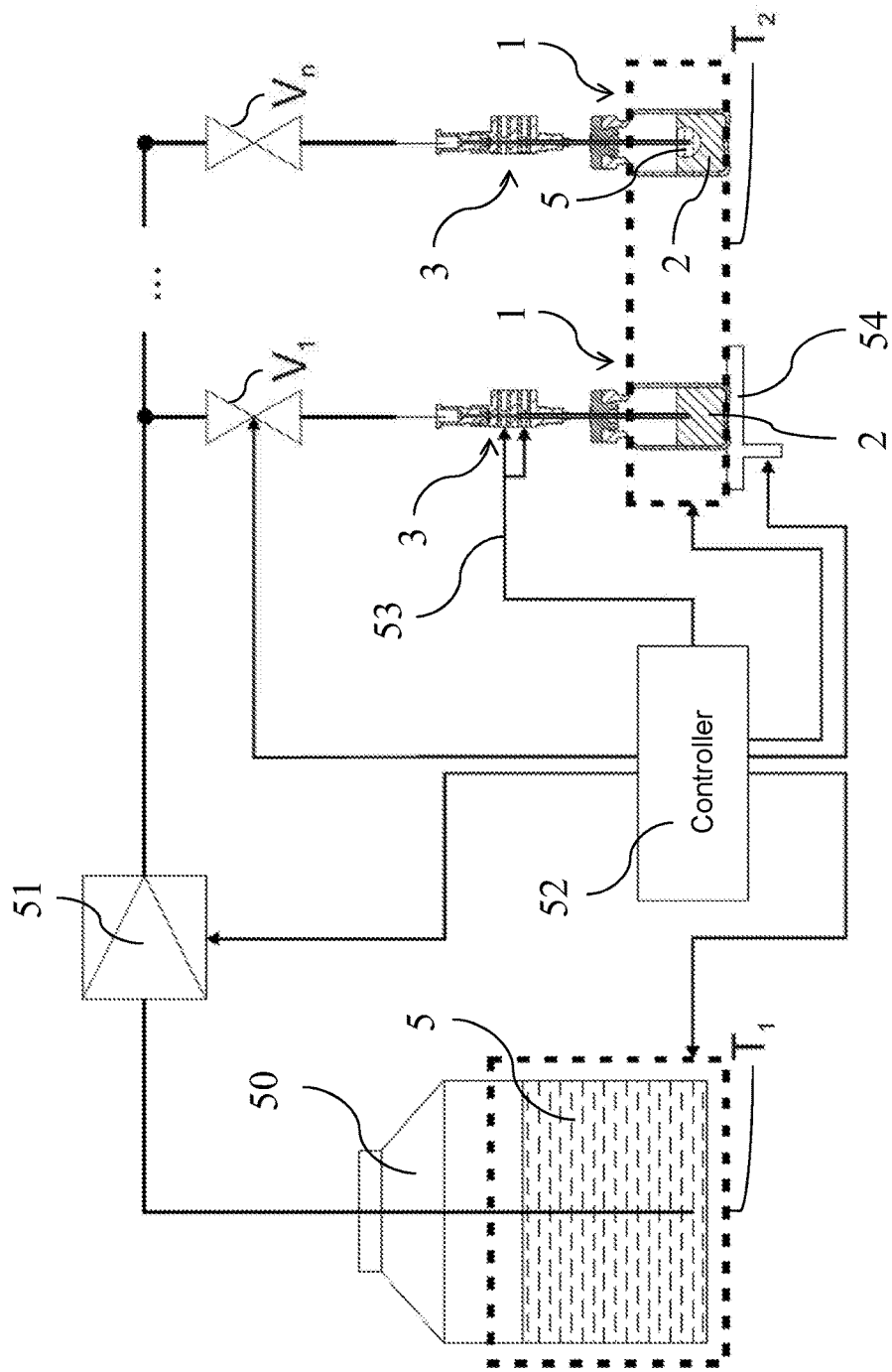
FIG. 8 shows an arrangement for preparing a plurality of reconstituted solutions in which additional parameters such as temperature can be adjusted.

Determination of the relationship of the impedance Z of a reconstituted solution having a specific concentration and the temperature may be performed, for example, as shown in FIG. 8. A plurality of vials 1 is schematically indicated, with each vial containing the same predetermined amount of the solid substance 2. A plurality of valves $V_1, \ldots, V_n$ are provided which are controlled such that a different amount of liquid solvent 5 is introduced through the inner tube of the respective electrode 3 (see FIG. 3) into the interior space of the respective vial 1 to prepare in each vial 1 a reconstituted solution of a specific concentration (different from the concentration of the solutions contained in the other vials). For that purpose, liquid solvent 5 can be fed from a reservoir 50 which may be heated/cooled to a first temperature $T_1$, for example, with the aid of a feed pump 51. A controller 52 is provided for controlling the respective valves $V_1, \ldots, V_n$ to ensure the proper amount of liquid solvent is added to the predetermined amount of the solid substance 2 contained in the respective vial 1 to obtain the reconstituted solutions having the different concentrations. The respective electrodes 3 are supplied with electrical power to cause the alternating current to flow through the electrode 3 as this has already explained in detail above, this being indicated by reference sign 53. The vials 1 can also be heated to the same temperature $T_1$, at which the impedances Z of the solutions with the different concentrations are then measured in the manner described above, but in a subsequent measurement the impedances Z are measured with the various solutions being heated to a different temperature $T_2$, and this impedance measurement can be repeated for the various solutions having the different concentrations at a plurality of other temperatures. Thus, the relationship between the impedance Z and the temperature can be determined for the solutions having the various concentrations. If during the preparation of the solution the vials 1 must be moved (e.g. gently shaken) in accordance with a predetermined movement pattern, this can be performed with the aid of a suitable moving unit 54. Measurement of the impedance Z of a solution can be performed during periods of the movement pattern in which the vial 1 is not moved. Measurement of the impedance Z of a solution can, however, also be performed during periods of the movement pattern in which the vial 1 is moved. All actions are performed under the control of the controller 52.

Knowing the relationship between the impedance Z of a solution at various concentrations and the temperature could allow prediction from a known reconstitution time of a solution at a known temperature of the reconstitution time of the same solution at a different temperature (since the relationship between temperature and impedance is known). A table of reconstitution times can then be provided by the manufacturer depending on the temperature at which the solution to be reconstituted is actually prepared. This may be advantageous since the liquid solvent (e.g. water for injection) may be provided at a desired temperature so that the solution can be conveniently injected at this temperature.

While the invention has been explained with the aid of embodiments, the invention is not limited to these embodiments. Rather, variations and alternatives are conceivable without departing from the teaching of the invention. Therefore, the scope of protection is defined by the appended claims.

The invention claimed is:

1. A method for determining whether reconstitution of a solution in a container is completed, the method comprising the steps of:
    selecting a predetermined amount of a solid substance and a predetermined amount of a liquid solvent from which the reconstituted solution is to be prepared, the predetermined amount of the solid substance and of the liquid solvent being selected such that the reconstituted solution is below its saturation limit,
    preparing a solution by solving in the container the predetermined amount of the solid substance in the predetermined amount of the liquid solvent,
    measuring a value chosen from impedance (Z) or resistance (R) of the solution in the container,
    determining whether a change of the measured value within a measuring time interval of a predetermined duration is below a defined threshold, and
    determining that reconstitution of the solution is completed and that the reconstituted solution is formed when the change of the measured value within the measuring time interval of the predetermined duration is below the defined threshold.

2. A method according to claim 1, wherein the value is the impedance (Z) of the solution.

3. A method according to claim 1, wherein the value is the resistance (R) of the solution.

4. A method according to claim 1, wherein the change of the measured value within the measuring time interval of the predetermined duration is below the threshold of 0.01%-5%.

5. A method according to claim 1, further comprising the steps of:
    determining a reconstitution time ($t_R$) of the solution in the container to be the duration between the time of starting to prepare the solution and the time at which the change of the measured impedance (Z) or resistance (R) of the solution is below the defined threshold within the measuring time interval of the predetermined duration.

6. A method according to claim 1, wherein the solid substance to be solved in the liquid solvent comprises an active pharmaceutical ingredient.

7. A method according to claim 1, wherein the solid substance to be solved in the liquid solvent is a lyophilisate.

8. A method according to claim 1, further comprising the step of setting the temperature of the solid substance and/or the temperature of the solvent and/or the temperature of the container to a respective predetermined temperature for preparing the reconstituted solution.

9. A method according to claim 1, further comprising the step of moving the container in accordance with a predetermined movement pattern during solving the solid substance in the liquid solvent.

10. A method according to claim 9, wherein measuring the impedance (Z) or resistance (R) of the solution in the container is performed only during portions of the movement pattern in which the container is not moved.

11. A method according to claim 5, further comprising the steps of:
before determining the reconstitution time ($t_R$) of the solution prepared from the predetermined amount of the solid substance and the predetermined amount of the liquid solvent, measuring the impedances (Z) or resistances (R) of a plurality of reconstituted solutions prepared from the same solid substance and the same liquid solvent, the individual reconstituted solutions of the plurality of reconstituted solutions having different concentrations of the solid substance solved in the respective individual reconstituted solution,
from the measurement of the impedances (Z) or resistances (R) of the plurality of reconstituted solutions determining a relationship between the impedance (Z) or the resistance (R) and the concentration (c) of the solid substance solved in this solution, and
determining the dissolution behavior over time during solving the predetermined amount of the solid substance in the predetermined amount of liquid solvent by assigning the respective measured impedance (Z) or resistance (R) of the solution to the respective concentration (c) in accordance with the determined relationship between the impedance (Z) or resistance (R) and the concentration (c) of the solid substance solved in the solution.

12. A method according to claim 11, further comprising the steps of:
before determining the reconstitution time ($t_R$) of the solution prepared from the predetermined amount of the solid substance and the predetermined amount of the liquid solvent, measuring the impedance (Z) or resistance (R) of each individual reconstituted solution of the plurality of reconstituted solutions at a plurality of different temperatures ($T_i$), and
from the measurement of the impedance (Z) or resistance (R) of the individual reconstituted solutions at the different temperatures ($T_i$) determining a relationship between the impedance (Z) or resistance (R) of the respective individual solution and the temperature.

13. A method according to claim 1, wherein the step of measuring in the container the impedance (Z) or resistance (R) of the solution comprises:
providing an electrode) having an electrically conductive inner tube and an electrically conductive outer tube, the outer tube surrounding the inner tube and being electrically isolated from the inner tube,
arranging the distal end of the electrode comprising the distal ends of the outer tube and the inner tube in the container in a manner such that the distal ends of the outer tube and of the inner tube are immersed in the solution during determination of the reconstitution time ($t_R$) of the solution,
supplying an alternating current ($I_S$) of a predetermined amperage to either the inner tube or the outer tube at a supply location of the electrode outside the container,
measuring the amperage of the alternating current ($I_S$) supplied to either the outer tube or the inner tube of the electrode,
measuring an alternating voltage ($V_S$) between the outer tube and the inner tube of the electrode, and
calculating the impedance (Z) or resistance (R) of the solution from the measured alternating voltage ($V_S$) between the outer tube and the inner tube and from the measured amperage of the alternating current ($I_S$) supplied to either the outer tube or the inner tube.

14. A method according to claim 13, wherein the step of preparing the solution by solving in the container the predetermined amount of the solid substance in the predetermined amount of the liquid solvent comprises the steps of:
providing in the container the predetermined amount of the solid substance,
providing a feeding port at the proximal end of the inner tube of the electrode, the feeding port being in fluid communication with the interior of inner tube, and
feeding the predetermined amount of the liquid solvent through the feeding port and the interior of the inner tube into the container to prepare the solution in the container.

* * * * *